United States Patent
Ogawa et al.

(10) Patent No.: US 6,852,670 B1
(45) Date of Patent: Feb. 8, 2005

(54) METHOD FOR MANUFACTURING ANION-LAYERED DOUBLE HYDROXIDE INTERCALATION COMPOUNDS AND COMPOUNDS PRODUCED THEREBY

(75) Inventors: Makoto Ogawa, Tokyo (JP); Shiho Asai, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 09/958,335

(22) PCT Filed: Nov. 4, 1999

(86) PCT No.: PCT/JP99/06134

§ 371 (c)(1),
(2), (4) Date: Feb. 6, 2002

(87) PCT Pub. No.: WO00/59629

PCT Pub. Date: Oct. 12, 2000

(30) Foreign Application Priority Data

Apr. 6, 1999 (JP) .......................................... 11/098867

(51) Int. Cl.[7] ............................ C01B 13/00; C09K 3/00
(52) U.S. Cl. ....................... 502/401; 502/506; 502/512; 252/184
(58) Field of Search ................................ 502/401, 506, 502/512; 252/184

(56) References Cited

U.S. PATENT DOCUMENTS

| | | | | |
|---|---|---|---|---|
| 4,629,626 A | * | 12/1986 | Miyata et al. | ............... 424/647 |
| 5,079,203 A | * | 1/1992 | Pinnavaia et al. | ............. 502/84 |
| 5,385,876 A | * | 1/1995 | Schwarz et al. | ............... 502/80 |
| 5,539,135 A | * | 7/1996 | Breuer et al. | ............... 554/167 |

* cited by examiner

Primary Examiner—Steven Bos
(74) Attorney, Agent, or Firm—Rader, Fishman & Grauer PLLC

(57) ABSTRACT

The present invention is a manufacturing method for an anion-layered double hydroxide intercalation compound that uses metal hydroxides as the stating material of the layered double hydroxides (LDH) which are the host material and allows sterically complicated and large-size anion compounds to be used as the guest material, and it has the characteristics such that a reaction mixture of the metal hydroxides and anion compound is heated and hydrothermally reacted in the absence of anion components other than the anion compound of the guest material. In addition, the present invention pertains to an anion-layered double hydroxide intercalation compound that uses bile acid as the anion compound of the guest material, which is effective as the carrier of medical drugs or as the absorbent of physiological active materials.

8 Claims, 1 Drawing Sheet

METHOD FOR MANUFACTURING ANION-LAYERED DOUBLE HYDROXIDE INTERCALATION COMPOUNDS AND COMPOUNDS PRODUCED THEREBY

FIELD OF INVENTION

The present invention relates to a manufacturing method for an anion-layered double hydroxide intercalation compound for which the host material is a layered double hydroxide (LDH), and the guest material is an anion compound, and more precisely, a manufacturing method for an anion-layered double hydroxide intercalation compound characterized by having a reaction compound heated and hydrothermally reacted in the absence of an anion compound other than the guest anion compound using metal hydroxides as the starting material of the layered double hydroxide, and additionally having a bile acid-layered double hydroxide intercalation compound in which the bile acid is introduced between the layers of the layered double hydroxides.

BACKGROUND OF THE INVENTION

Inorganic-organic compounds obtained by placing an organic compound between layers of inorganic layered material have the potential to demonstrate characteristics that cannot be achieved by an individual host or guest, due to the interaction of the inorganic and organic layer. Layered double hydroxides (hereinafter referred to as LDH) represented by hydrotalcite are the host material of hope, because they have characteristics not found in other layered materials, such as, the anion can be placed in between layers and it can be synthesized under relatively non-severe conditions. (Makoto Ogawa, et al. "Surface", 32 (11), 695, (1994)).

These intercalation compounds that are obtained through intercalation in which the guest material is inserted between layers of inorganic layered material are inorganic-organic nano double materials that have a structure such that a nanometer order of thickness of the host layers and guest layers are alternately laminated. The guest exists in the two-dimensional nano-space called the intercalation, and it has a distinctive state due to the interaction between the host-guest or guest-guest. In addition to the basic scientific interest in these interactions and micro-structures that are derived from such development in this area of material design has attracted a great deal of attention. A wide range of potential, such as, as an absorbent, catalyst, ion exchange material, and ion conductor has already been pointed out. (Makoto Ogawa "Catalyst", 39 (7), 557, (1997)).

The LDH having an anion in between the layers demonstrates characteristics that other layered materials do not have. Therefore, the synthesis of LDH intercalation compounds using an organic anion as the guest has been investigated using such techniques as the coprecipitation method, the ion exchanging method, and the reconstruction method. As an organic acid guest compound, surfactants such as an alkyl sulfate or a fatty acid, aromatic hydrocarbon carboxylic acid compounds such as phthalic acid or benzoic acid, and pigment compounds such as indigo carmine are known.

Deoxycholic acid (hereinafter referred to as DCA) is one of the bile acids and a surfactant that carries cholesterols in organisms. Its association state is still unclear and the structure of layered compounds using this as a guest is very interesting.

Therefore, the present inventors attempted the synthesis of a deoxycholic acid-layered double hydroxide intercalation compound (LDH-DCA layered compound) using coprecipitation and the ion exchanging method. However, with these methods of the prior art, it was difficult to place the DCA in between the layers. It was assumed that the difficulty is due to the DCA being sterically complicated and having a large size so that the selectivity of the ion exchange is low and it is hindered by the coexisting anions.

DISCLOSURE OF THE INVENTION

The present invention is directed to a new synthesizing system in which anions other than the guest do not exist, by using such hydroxides as those of magnesium and aluminum as a starting material, and consequently achieving the synthesis of LDH-DCA intercalation compounds.

Broadly stated, the present invention provides a manufacturing method for a new anion-layered double hydroxide intercalation compound. More precisely, the present invention provides a manufacturing method for an anion-layered double hydroxide intercalation compound in which even sterically complex and large size anions can be introduced in between the layers of the layered double hydroxides.

The present invention further provides a new bile acid-layered double hydroxide intercalation compound in which bile acid is introduced in between the layers of layered double hydroxides.

More precisely, the present invention provides a new deoxycholic acid-layered double hydroxide intercalation compound, in which a layered double hydroxide (LDH) represented by hydrotalcite is used as a host material, and deoxycholic acid (DCA) which is one of the bile acids introduced as a guest material in between the layers, and a method of making the same.

PREFERRED EMBODIMENT OF THE INVENTION

Figure 1:
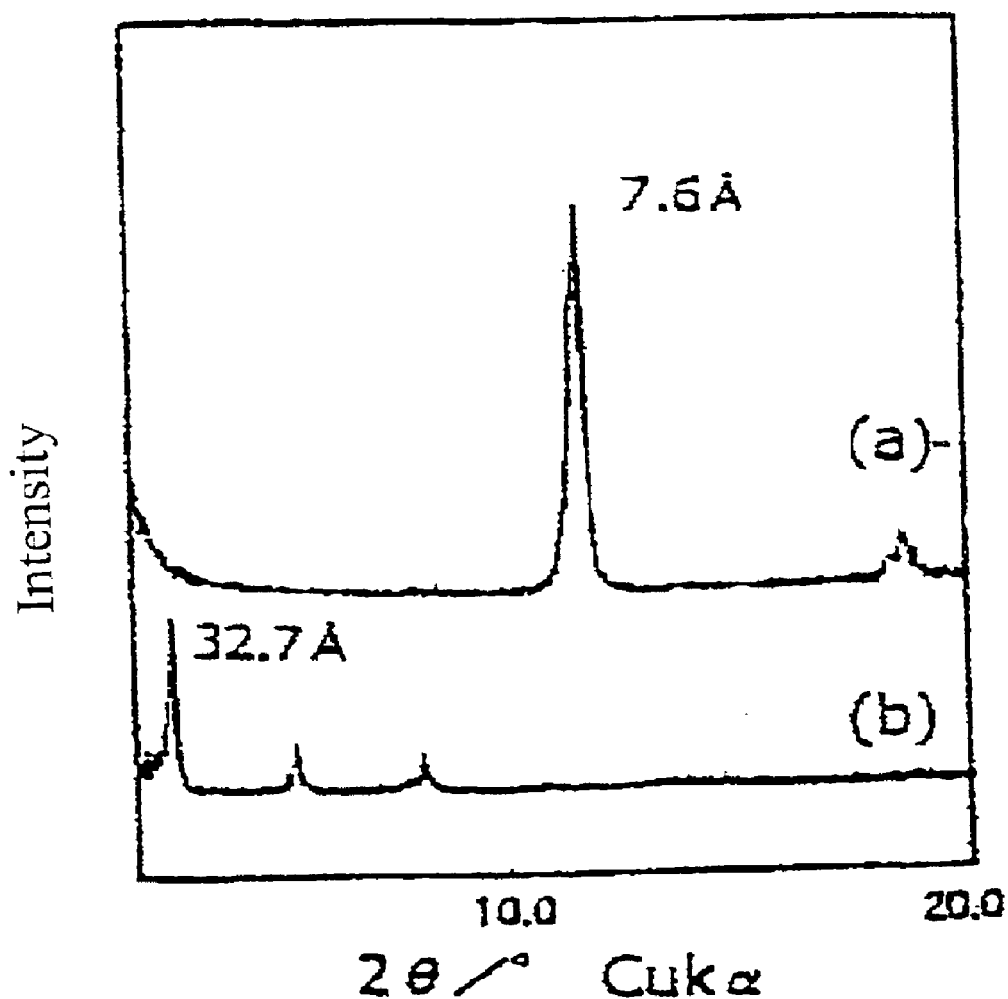
FIG. 1 shows an X-ray diffraction pattern of the anion-layered double hydroxide intercalation compound of the present invention. (a) shows the case in which sodium carbonate is used as the guest and (b) shows the case in which DCA is used as the guest.

The present invention relates to a manufacturing method for anion-layered double hydroxide intercalation compounds using layered double hydroxides (LDH) as a host material and an anion compound as a guest material wherein, metal hydroxides are used as the starting material of the layered double hydroxides, and the host material and guest material compounds in the reaction mixture are heated and hydrothermally reacted in the absence of anion components other than the anion compound of the guest material.

In addition, the present invention pertains to a bile acid-layered double hydroxide intercalation compound.

Inorganic layered double hydroxides are preferable as the layered double hydroxide of the present invention. The desirable formula of the layered double hydroxides is shown as follows:

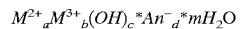

$$M^{2+}{}_a M^{3+}{}_b (OH)_c {}^* An^-{}_d {}^* mH_2O$$

In the formula, $M^{2+}$ shows a dinuclear metal atom and $M^{3+}$ shows a trinuclear metal atom. An represents an anion and a, b, c and d show the number of atoms or atomic groups, and m shows the number of $H_2O$ molecules.

Examples of preferable dinuclear metal atoms for the LDH of the present invention are, Mg, Ni, Fe, Zn, Cu, Co, Mn, Ca, etc. More preferably, Mg can be used. Examples of preferable trinuclear metal atoms are Al, Cr, Co, Fe, Mn, Ni, La, etc. More preferably, Al can be used. Examples of preferable anions (An-) are inorganic anions such as $CO_3^{2-}$, $SO_4^{2-}$, $OH^-$, and organic anions which are induced from organic acids such as organic carboxylic acid, organic sulfonic acid and bile acids.

An example of the layered double hydroxides of the present invention is hydrotalcite and an example of the formula of the natural LDH is as follows:

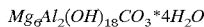

$$Mg_6Al_2(OH)_{18}CO_3 \cdot 4H_2O$$

As the bile acid for the present invention, deoxycholic acid is preferable.

The LDH-DCA intercalation compound of the present invention is a new compound in that it is an intercalation compound in which DCA, a surfactant that carries cholesterols in organisms, is the guest. Therefore, the application as a carrier for medical drugs or an absorbent of physiological active materials can be considered and there is hope it will yield an effective fine material.

The characteristics of the manufacturing method of the anion-layered double hydroxide intercalation compound of the present invention is such that metal hydroxides are used as the starting material of the layered double hydroxides, and an anion-layered double hydroxide intercalation compound is manufactured in the absence of anion components other than the anion compound of the guest material. This method allows the introduction of dimensionally complicated guest anions or large-sized guest anions between the layers of layered double hydroxides.

Examples of metal hydroxide materials are the above-described dinuclear or trinuclear metal hydroxides, such as magnesium hydroxide, aluminum hydroxide, nickel hydroxide, cobalt hydroxide, iron hydroxide, etc. In order to manufacture the above-mentioned hydrotalcite, the use of magnesium hydroxide or aluminum hydroxide is preferable.

For the reactive conditions of the manufacturing method of the anion-layered double hydroxide intercalation compound of the present invention, traditional hydrothermal reactions are acceptable, however, it is desirable to have the hydrothermal reaction under pressure such as in an autoclave.

An example of the manufacturing method of the present invention is one in which magnesium hydroxide and aluminum hydroxide are suspended in water, and an anion component such as DCA is added and sufficiently agitated, and then it is heated at 150° C. for 24 hours and chilled, suction filtered, rinsed with, for example, ethanol and dried at 70° C. and then the target material can be obtained.

The ratio of the dinuclear metal hydroxide and the trinuclear metal hydroxide can be appropriately selected depending on the value of a or b in the above-mentioned formula for the target intercalation compound. In the above-mentioned example with magnesium hydroxide and aluminum hydroxide, the desirable Mg/Al ratio is 1 to 6 and more preferably, 3 to 5. The amount of anion component can be appropriately selected depending on the amount added to the between layers. In the case of the above-mentioned DCA, it is 1 to 10 mol compared to the aluminum atoms, and more preferably, 3 to 7 mol.

The temperature of the hydrothermal reaction is acceptable as long as it is a temperature at which the reaction fully advances, and preferably it is 80° C. or more and more preferably it is 100 to 200° C. A more desirable temperature is 120 to 160° C.

After the hydrothermal reaction, the target object can be isolated and purified using standard methods.

In order to confirm that the anion-layered double hydroxide intercalation compound of the target is generated using the method of the present invention, the synthesis of an LDH intercalation compound is carried out using magnesium hydroxide and aluminum hydroxide as starting materials and sodium carbonate and deoxycholic acid as the guests.

For both cases, when sodium carbonate is used as the guest, and DCA is used as the guest, the product was obtained as a white precipitate. The X-ray diffraction pattern for both cases are shown in FIGS. 1(a) and (b). The basic interplaner spacing of the product when sodium carbonate is used was 7.6 angstroms. This is approximately equal to the value of the basic interplaner spacing of the carbonate-type LDH synthesized through the ion exchanging method and coprecipitation method. From this fact, it was confirmed that the LDH was synthesized using the method of the present invention.

The basic interplaner spacing of the product when DCA is used as the guest was 32.7 angstroms and its higher order reaction was observed indicating that the product had the layer structure. Given the fact that the thickness of the blue site layer is 4.8 angstroms, it can be assumed that the DCA was taken in between the layers. In addition, the infrared absorption spectrum shows the absorption band (1560 cm$^{-1}$) that is attributed to the stretching vibration of the $COO^-$, indicating that DCA exists in a form of an anion in between the layers.

Thermogravimetric analysis shows the reduction of the weight having an initiation point around 300° C. and the DTA curve shows the heating peak around the same temperature. The value of the weight reduction shows that the DCA is taken in at approximately a 1:1 ratio relative to the aluminum.

From the facts described above, the synthesis of a deoxycholic acid-layered double hydroxide intercalation compound was confirmed. The method of the present invention is effective as a new synthesizing method of LDH intercalation compounds that cannot be synthesized through the coprecipitation or ion exchanging method.

Embodiments

The present invention is described in detail using embodiments as follows. In any event the present invention is not limited by these embodiments.

Embodiment 1

Using magnesium hydroxide and aluminum hydroxide as the starting materials, and sodium carbonate as the guest, the synthesis of an LDH intercalation compound was carried out. It was prepared so that the ratio of the magnesium hydroxide and the aluminum hydroxide was Mg/Al=4, and the ratio of the guest material and the aluminum hydroxide became NalCO$_3$/Al=1. It was dispersed in deionized water and maintained in a Teflon-coated barrel-shaped container at 150° C. for 24 hours. After it was chilled to room temperature, it was suction filtered, rinsed with ethanol and then, dried at 70° C.

The evaluation of the product was carried out using powder X-ray diffraction analysis, an infrared absorption spectrum, thermal analysis and SEM.

Embodiment 2

Using magnesium hydroxide and aluminum hydroxide as the starting materials, and deoxycholic acid as the guest, the synthesis of an LDH intercalation compound was carried out. It was prepared so that the ratio of the magnesium hydroxide and the aluminum hydroxide was Mg/Al=4, and the ratio of the guest material and the aluminum hydroxide became DCA/Al-=5. It was dispersed in deionized water and maintained in a Teflon-coated barrel-shaped container at 150° C. for 24 hours. After it was chilled to room temperature, it was suction filtered, rinsed with ethanol and then, dried at 70° C.

The evaluation of the product was carried out using powder X-ray diffraction analysis, an infrared absorption spectrum, thermal analysis and SEM.

Field of Industrial Application

The present invention provides a new manufacturing method for anion-layered double hydroxide intercalation compounds. The present invention allows for ease in the introduction of sterically complicated anions and large-sized anions in between the layers of layered double hydroxides.

In addition the present invention provides a new LDH-DCA intercalation compound. DCA is a surfactant that carries cholesterol in organisms. Therefore the LDH-DCA intercalation compound of the present invention can provide a fine material that is effective as the carrier of medical drugs and as an absorbent of physiological active materials.

What is claimed is:

1. A method for manufacturing an anion-layered double hydroxide intercalation compound comprising steps of:

providing a layered double hydroxide (LDH) as a host material;

providing an anion compound made of an organic acid as a guest material;

providing metal hydroxide as a starting material of the LDH;

mixing a bile acid as the guest material with the host material to make a reaction mixture; and heating and hydrothermally reacting the reaction mixture in the absence of anion components other than the anion compound of the guest material and LDH of the host material.

2. A method in accordance with claim 1, wherein the hydrothermally reacting step is carried out under pressure.

3. A method in accordance with claim 1, wherein the metal hydroxide is one or more of magnesium hydroxide and aluminum hydroxide.

4. A method in accordance with claim 1, wherein the layered double hydroxide is hydrotalcite.

5. A method in accordance with claim 1, wherein the anion compound is deoxycholic acid.

6. A bile acid-layered double hydroxide intercalation compound, wherein the bile acid is introduced in between the layered double hydroxides.

7. A bile acid-layered double hydroxide intercalation compound in accordance with claim 6, wherein the bile acid is deoxycholic acid.

8. A bile acid-layered double hydroxide intercalation compound in accordance with claim 6, wherein the layered double hydroxide is hydrotalcite.

* * * * *